(12) United States Patent
Giust et al.

(10) Patent No.: US 9,550,716 B2
(45) Date of Patent: Jan. 24, 2017

(54) PROCESS FOR TREPROSTINIL SALT PREPARATION

(75) Inventors: Walter Giust, Toronto (CA); Fabio Souza, Mississauga (CA); Jan Oudenes, Aurora (CA); Boris Gorin, Oakville (CA); Elena Bejan, Brantford (CA)

(73) Assignee: EON LABS, INC., Princeton, NJ (US)

( * ) Notice: Subject to any disclaimer, the term of this patent is extended or adjusted under 35 U.S.C. 154(b) by 249 days.

(21) Appl. No.: 13/520,872

(22) PCT Filed: Dec. 22, 2011

(86) PCT No.: PCT/CA2011/050804
§ 371 (c)(1),
(2), (4) Date: Oct. 8, 2013

(87) PCT Pub. No.: WO2012/088607
PCT Pub. Date: Jul. 5, 2012

(65) Prior Publication Data
US 2014/0024856 A1 Jan. 23, 2014

(30) Foreign Application Priority Data
Dec. 30, 2010 (CA) .................................. 2726599

(51) Int. Cl.
*C07C 51/43* (2006.01)
*C07C 51/41* (2006.01)

(52) U.S. Cl.
CPC ............. *C07C 51/412* (2013.01); *C07C 51/43* (2013.01)

(58) Field of Classification Search
None
See application file for complete search history.

(56) References Cited

U.S. PATENT DOCUMENTS

| | | | |
|---|---|---|---|
| 4,306,075 A | 12/1981 | Aristoff | |
| 4,486,598 A | 12/1984 | Aristoff | |
| 4,537,346 A | 8/1985 | Duprez | |
| 5,810,071 A | 9/1998 | Pavlin | |
| 5,950,715 A | 9/1999 | Jonsson et al. | |
| 6,182,749 B1 | 2/2001 | Brost et al. | |
| 6,441,245 B1 | 8/2002 | Moriarty et al. | |
| 6,700,025 B2 | 3/2004 | Moriarty et al. | |
| 6,765,117 B2 | 7/2004 | Moriarty et al. | |
| 6,809,223 B2 | 10/2004 | Moriarty et al. | |
| 7,371,888 B2 | 5/2008 | Zhao et al. | |
| 7,417,070 B2 † | 8/2008 | Phares et al. | |
| 2008/0249167 A1 * | 10/2008 | Phares et al. | 514/532 |
| 2009/0163738 A1 | 6/2009 | Batra et al. | |
| 2011/0319641 A1 | 12/2011 | Batra et al. | |
| 2012/0197041 A1 | 8/2012 | Batra et al. | |

FOREIGN PATENT DOCUMENTS

| | | |
|---|---|---|
| CA | 1201712 | 3/1986 |
| CA | 2 307 163 C | 5/1999 |
| CA | 2 847 985 A1 | 5/1999 |
| CA | 2 698 721 A1 | 3/2009 |
| CA | 2777070 | 12/2011 |
| CA | 2710726 | 1/2012 |
| EP | 1 611 320 B1 | 12/2010 |
| WO | 2004/092552 A2 | 10/2004 |
| WO | 2011153363 | 12/2011 |
| WO | 2012009816 | 1/2012 |
| WO | 2012/088607 | 7/2012 |

OTHER PUBLICATIONS

Danishefsky et al., J. Am. Chem. Soc., 107:1421-1423 (1985). "The total synthesis of Quinocarcinol Methyl Ester."
Gould et at., International Journal of Pharmaceutics 33:201-217 (1986). "Salt selection for basic drugs."
Green et al., "Protective groups in organics synthesis: Protection for theHydroxyl group, including 1,2- and ,3 diols", pp. 86-90, (1999). Third Edition.
Horita et al. Tetrahedron 42(11):3021-3028 (1986). "On the selectivity of deprotection of benzyl, mpm 94-methoxybenzyl) and dmpm (3,4-dimethoxybenzyl) protecting groups for hydroxy functions."
Moriarty et al., J. Org. Chem. 69:1890-1902 (2004). "The Intramolecular Asymmetric pauson-khand cyclizatin as a novel and general stereoselective route to benzindene prostacyclins: synthesis of UT-15 treprostinil."
Stahl et al., Handbook on Pharmaceutical salts: Properties, selection, and use., pp. 214-216, 314, 315 and 322, (2002).
International Preliminary Report on Patentabilty on PCT/CA2011/050451, dated Dec. 20, 2012.
Written Opinion of the International Search Authority PCT/CA2011/050448, dated Sep. 15, 2011.
Office Action, Third Party Submission under 37 CFR 1.290, Dated Mar. 21, 2014, pp. 1-151, U.S. Appl. No. 13/811,301.
Office Action, Third Party Submission under 37 CFR 1.290, Dated Mar. 21, 2014, pp. 1-32, U.S. Appl. No. 13/520,872.
Li, J., et al., "Synthetic approaches to the 2002 new drugs" Mini reviews in Medicinal Chemistry, 2004, 207-233.
Lukac et al. "The methoxybenzyl ethers as useful protecting groups for hydroxy compounds: methods of deprotection." Acta Facultatis Pharmaceuticae Universitatis Comenianae; Tomus LII, 2005, p. 31-32.
Remodulation Injection Package Insert.
U.S. Appl. No. 61/351,115, filed Jun. 3, 2010.
U.S. Appl. No. 13/435,720, filed Mar. 30, 2012.
U.S. Appl. No. 13/151,465, filed Jun. 2, 2011.
U.S. Appl. No. 13/811,301, filed Aug. 30, 2013.
U.S. Appl. No. 13/811,305, filed Mar. 28, 2013.

(Continued)

*Primary Examiner* — Sudhakar Katakam
*Assistant Examiner* — Jennifer C Sawyer
(74) *Attorney, Agent, or Firm* — Nixon Peabody LLP

(57) ABSTRACT

Disclosed is a process for preparing a treprostinil salt. The process involves the step of dissolving treprostinil in a water-miscible organic solvent to form a treprostinil solution. The treprostinil solution is reacted with an aqueous basic solution containing an alkali metal cation to form treprostinil salt. Allowing crystallization of the treprostinil salt to take place, and then collecting the treprostinil salt formed.

34 Claims, 1 Drawing Sheet

(56) References Cited

OTHER PUBLICATIONS

Danishefsky et al. "The total synthesis of quinocarcinol methyl ester." J. of the American Chemical Society, 1985, vol. 107, 1421-1423.
Gould, "Salt selection for basic drugs," International Journal of Pharmaceutics, 1986, 33:201-217.†
Stahl et al., Handbook of Pharmaceutical Salts, 2002, pp. 214-216, 314, 315 and 322.†

\* cited by examiner
† cited by third party

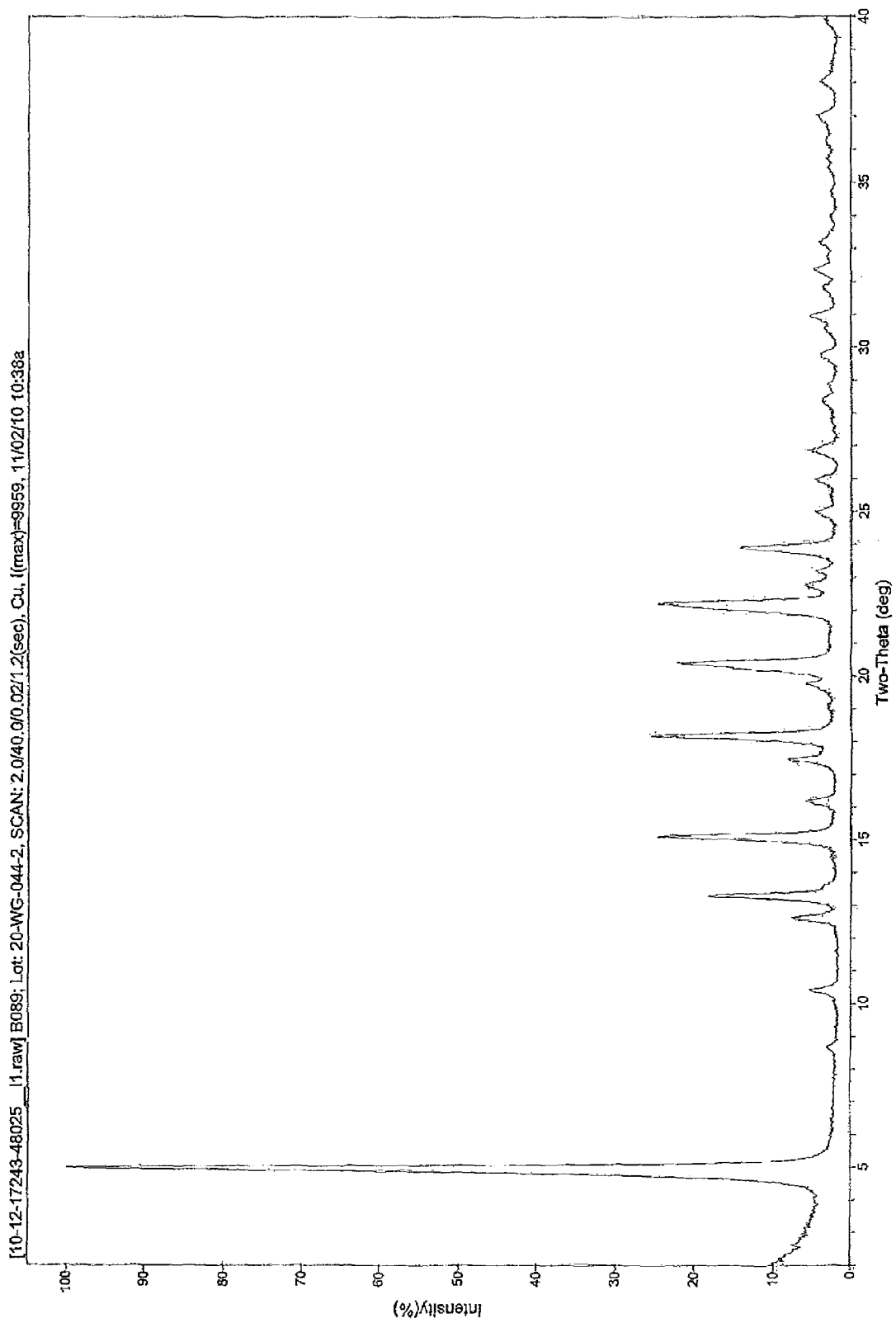

PROCESS FOR TREPROSTINIL SALT PREPARATION

CROSS REFERENCE TO RELATED APPLICATIONS

This application is a 35 U.S.C. §371 National Stage Entry Application of International Application No. PCT/CA2011/050804, filed Dec. 22, 2011, which designates the U.S., and which claims benefit under 35 U.S.C. §119(b) of Canadian Patent Application No. 2,726,599, filed Dec. 30, 2010, the content of the above patent application is hereby expressly incorporated herein by reference into the detailed description hereof in its entirety.

TECHNICAL FIELD

This specification relates to a process for treprostinil salt preparation.

BACKGROUND

Prostacyclin derivatives are useful pharmaceutical compounds possessing pharmacological activities such as platelet aggregation inhibition, gastric secretion reduction, lesion inhibition, vasodilation and bronchodilation. Treprostinil is a prostacyclin analogue, having the following chemical structure:

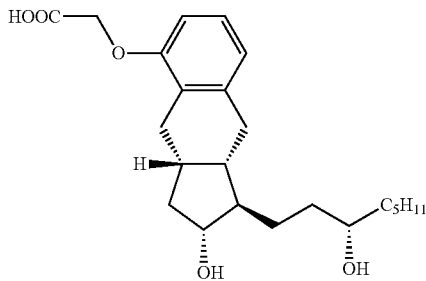

Treprostinil sodium solution is marketed as Remodulin® and Tyvaso® for treatment of pulmonary arterial hypertension.

Process for preparation of treprostinil, treprostinil derivatives and intermediates useful in preparation of treprostinil are described in U.S. Pat. Nos. 4,306,075; 6,700,025; 6,809,223 and 6,765,117. U.S. Pat. No. 4,306,075 (col. 40, l. 41-62) discloses a general procedure for preparation of pharmacologically acceptable salts of treprostinil, where preparation of an inorganic salt of treprostinil can be carried out by dissolution of treprostinil in water, followed by neutralization with appropriate amounts of corresponding inorganic base. However, a commercially viable synthetic route for preparation of the sodium salt of treprostinil is desired.

Preparation of treprostinil sodium can be difficult, as the salt is soluble in water and difficult to precipitate, while the treprostinil acid is only sparingly soluble in water. Salts of a compound can be useful due in part to their increased stability, bioavailability and solubility in water. Availability of treprostinil salt can also help in preparation of a formulation, including a pharmaceutical formulation.

Therefore, there is a need in the art for a process for the preparation of a salt of treprostinil. Moreover, there is a need the art for a process for the synthesis of treprostinil sodium, including a commercially viable process.

SUMMARY OF THE INVENTION

In one aspect, the specification relates to a process for preparing a treprostinil salt, comprising:
dissolving treprostinil in a water-miscible organic solvent to form a treprostinil solution;
reacting the treprostinil solution with an aqueous basic solution containing an alkali metal cation to form a reaction mixture containing the treprostinil salt;
allowing crystallization of the treprostinil salt; and
collecting the treprostinil salt formed.

BRIEF DESCRIPTION OF THE DRAWINGS

FIG. 1 shows a powder X-ray diffraction spectrum of treprostinil sodium obtained according to the reaction described herein.

DETAILED DESCRIPTION

As noted above, the specification relates to a process for preparing a treprostinil salt, the process containing the steps of:
dissolving treprostinil in a water-miscible organic solvent to form a treprostinil solution;
reacting the treprostinil solution with an aqueous basic solution containing an alkali metal cation to form a reaction mixture containing the treprostinil salt;
allowing crystallization of the treprostinil salt; and
collecting the crystals of the treprostinil salt.

The water-miscible organic solvent used for dissolving treprostinil is not particularly limited, and can contain one or more functional groups, as long as the organic solvent is miscible and can form a solution with water. In one embodiment, for example and without limitation, the water-miscible organic solvent is a water-miscible ketone solvent, water-miscible alcohol or water-miscible ether.

In one embodiment, for example and without limitation, the water-miscible organic solvent is a water-miscible ketone solvent. The number of carbon atoms in the water-miscible ketone solvent is not particularly limited but can be any number, as long as the water-miscible ketone solvent is miscible in water. In one embodiment, the water-miscible ketone solvent contains from 3 to 8 carbon atoms. In another embodiment, for example and without limitation, the water-miscible ketone solvent is a hydrocarbon based water-miscible ketone solvent. A hydrocarbon based water-miscible ketone solvent contains a ketone functional group and a hydrocarbon chain having carbon and hydrogen atoms. In a further embodiment, for example and without limitation, the water-miscible ketone solvent is a linear or branched alkyl ketone. The number of carbon atoms in the alkyl ketone is not particularly limited and contain, for example and without limitation, 3 to 6 carbon atoms. In one embodiment, for example and without limitation, the water-miscible solvent is acetone.

Examples of water-miscible ketone solvents for use in preparation of treprostinil salt can include, for example and without limitation, acetone, butanone, 2-pentanone, 3-pentanone, methyl isopropyl ketone, 2-hexanone, 3-hexanone, methyl isobutyl ketone (MIBK), ethyl isopropyl ketone, cyclopentanone, 2-methyl cyclopentanone, 3-methyl cyclopentanone, cyclohexanone and others.

In another embodiment, the water-miscible organic solvent is a water-miscible alcohol. The number of carbon atoms in the water-miscible alcohol is not particularly limited but can be any number, as long as the alcohol is miscible in water. In one embodiment, for example and without limitation, the water-miscible alcohol contains from 3 to 8 carbon atoms. In another embodiment, for example and without limitation, the water-miscible alcohol is a hydrocarbon based water-miscible alcohol. A hydrocarbon based water-miscible alcohol contains an alcohol functional group and a hydrocarbon chain having carbon and hydrogen atoms. In a further embodiment, for example and without limitation, the water-miscible alcohol is a linear or branched alkyl alcohol. The number of carbon atoms in the linear or branched hydrocarbon based alcohol is not particularly limited and contain, for example and without limitation, 3 to 6 carbon atoms. In one embodiment, for example and without limitation, the water-miscible alcohol is methanol, ethanol, propanol, isopropanol and others.

Similar to the water-miscible organic ketones solvent and water-miscible alcohols noted above, other water-miscible organic solvents can also be used. Examples of other water-miscible organic solvents can include, for example and without limitation, tetrahydrofuran, acetonitrile and others. In addition, two or more organic solvents can also be used so long the organic solvents together are miscible in water.

The ratio of treprostinil to the water-miscible organic solvent as described herein is not particularly limited. In one embodiment, for example and without limitation, the ratio of treprostinil to the water-miscible organic solvent is 1 g of treprostinil to from 5 to 50 mL of the water-miscible organic solvent. In another embodiment the ratio of treprostinil to the water-miscible organic solvent is, for example and without limitation, 1 g of treprostinil to from 15 to 30 mL of the water-miscible organic solvent.

The aqueous basic solution for reaction with treprostinil to form treprostinil salt contains an aqueous solution and a base, which can deprotonate carboxylic acid moiety of treprostinil. The base in the aqueous basic solution for use in the reaction described herein is not particularly limited and contains an anion and an alkali metal cation. In one embodiment, for example and without limitation, the anion is hydroxide, carbonate or bicarbonate anion. The alkali metal cation for use in the reaction described herein can be, for example and without limitation, lithium, sodium or potassium. Appropriate anion and alkali metal cation can be determined based on the reaction conditions and the desired treprostinil salt. In one embodiment, for example and without limitation, the aqueous basic solution contains sodium hydroxide for reaction with treprostinil to form treprostinil sodium.

The concentration of the base in the aqueous basic solution for reaction with treprostinil is not particularly limited. Sufficient concentration of the aqueous basic solution can be used to allow reaction with treprostinil and to allow formation of treprostinil salt. In one embodiment, for example and without limitation, the base in the aqueous basic solution has a concentration of from about 2 to about 8 molar. In another embodiment, for example and without limitation, the base in the aqueous basic solution has a concentration of from about 5 molar.

The mole ratio of the base in the aqueous basic solution to treprostinil in the treprostinil solution is not particularly limited. The mole ratio used can be chosen to maximize yield, by reaction of the base with treprostinil and allowing crystallization of treprostinil salt. In general, the ratio of the base to treprostinil used allows for deprotonation of treprostinil. In one embodiment, for example and without limitation, the mole ratio of base in the basic solution to treprostinil in the treprostinil solution ranges from 1:1 to 2:1. In another embodiment, the mole ratio of base in the basic solution to treprostinil in the treprostinil solution is, for example and without limitation, about 1.05:1, 1.1:1 or 1.2:1.

The volumetric ratio of the water-miscible organic solvent to the aqueous basic solution for preparation of treprostinil salt from treprostinil is not particularly limited. The volumetric ratio can be set to maximize yield and/or quality of treprostinil salt obtained. In one embodiment, for example and without limitation, the volumetric ratio of the water-miscible organic solvent to the aqueous basic solution is from 10:1 to 70:1. In another embodiment, the volumetric ratio of the water-miscible organic solvent to the aqueous basic solution is, for example and without limitation, about 40:1.

In one embodiment, the process for preparation of treprostinil salt from treprostinil is carried out by warming the treprostinil solution prior to reaction of the treprostinil solution with the aqueous basic solution. The temperature the treprostinil solution is warmed is not particularly limited. In one embodiment, for example and without limitation, the treprostinil solution is warmed up to about 60° C. prior to reacting it with the aqueous basic solution. In another embodiment, the treprostinil solution is warmed, for example and without limitation, up to about 30° C. prior to reacting it with the aqueous basic solution. The temperature the treprostinil solution is warmed can include all temperature values between those noted above.

The addition of reactants for performing the reaction of treprostinil in the treprostinil solution with the aqueous basic solution is not particularly limited. In one embodiment, for example and without limitation, the aqueous basic solution is added to the treprostinil solution for reaction with treprostinil.

The temperature for carrying out the reaction of treprostinil in the treprostinil solution with the aqueous basic solution is not particularly limited. In one embodiment, for example and without limitation, the reaction of the treprostinil solution with the aqueous basic solution is carried out at an internal temperature below about 60° C. In another embodiment, the reaction of the treprostinil solution with the aqueous basic solution is carried out at an internal temperature, for example and without limitation, below about 30° C. The temperature for carrying out the reaction can include all values between those noted above.

The reaction of treprostinil in the treprostinil solution with the aqueous basic solution as described herein can be carried out, for example and without limitation, by agitating the reaction. The rate of agitation for carrying out the reaction is not particularly limited. The rate of agitation can be set to maximize yield and/or quality of treprostinil salt. In one embodiment, for example and without limitation, agitation is continued even after allowing crystallization of treprostinil salt. The time period for the agitation is also not particularly limited and can be, for example and without limitation, for at least about 4 hours. In another embodiment, the agitation is carried out, for example and without limitation, for about 1 hour.

The temperature at which the reaction mixture is agitated after allowing crystallization of treprostinil salt and prior to collecting treprostinil salt is not particularly limited. In one embodiment, for example and without limitation, the reaction mixture is agitated at room temperature.

In another embodiment, the reaction mixture is cooled prior to collecting treprostinil salt. The temperature to which the reaction mixture is cooled prior to collecting treprostinil salt is not particularly limited and can be, for example and without limitation, from 0 to 15° C. In another embodiment, the temperature to which the reaction mixture is cooled prior to collecting treprostinil salt is, for example and without limitation, 0 to 5° C. In a further embodiment, agitation can continued during the cooling of the reaction mixture.

The time period for which the reaction mixture is cooled and/or agitated prior to collecting the crystals is not particularly limited. In one embodiment, for example and without limitation, the reaction mixture is cooled and agitated for about 5 hours. In another embodiment, the reaction mixture is cooled and agitated, for example and without limitation, about 1 hour.

The method of collecting treprostinil salt formed after completion of the reaction is not particularly limited. In one embodiment, for example and without limitation, treprostinil salt is collected by vacuum filtration. In another embodiment, treprostinil salt collected is dried.

In one embodiment, the treprostinil sodium can be obtained from intermediate 1, as shown in scheme 1. Intermediate 1 is alkylated then hydrolyzed to obtain treprostinil. The reaction product obtained after alkylation can be, for example and without limitation, an ester. The treprostinil obtained is dissolved in a water-miscible organic solvent and reacted with an aqueous basic solution, as described herein, to form treprostinil sodium. The treprostinil sodium is allowed to crystallize and then collected.

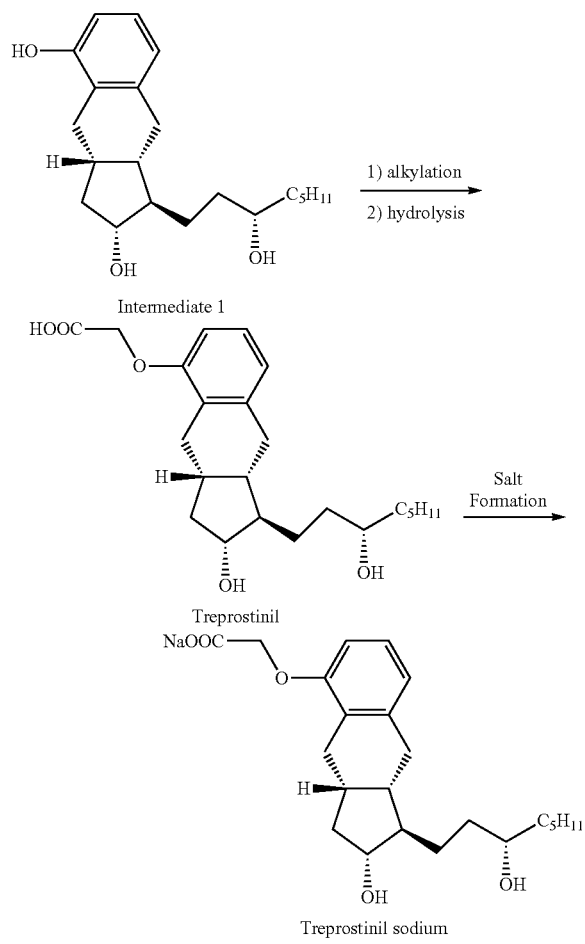

The alkylation method of intermediate 1 is not particularly limited and different methods can be used depending upon the synthetic route adopted. In one embodiment, for example and without limitation, intermediate 1 is alkylated using a halo-acetate or an acetate having a leaving group at the alkyl moiety. In a further embodiment, the halo-acetate can be, for example and without limitation, bromoacetate or chloroacetate.

The solvent for the alkylation reaction is not particularly limited and can be determined. In one embodiment, for example and without limitation, the alkylation reaction is carried out in acetone. In addition, the time and temperature for carrying out the alkylation reaction are also not particularly limited, and can be determined. In one embodiment, for example and without limitation, the reaction was carried out for about from 5 to 10 hours. In another embodiment, the reaction temperature can be, for example and without limitation, room temperature or from room temperature to about 50° C. Upon completion, the reaction is worked up and purified using standard methodology to obtain treprostinil.

EXAMPLES

The following examples are illustrative and non-limiting and represent specific embodiments of the present invention.

Example 1

Treprostinil Preparation

A mixture of Intermediate 1 (3.8 g; 11.3 mmoL), methyl bromoacetate (2.2 g; 14.1 mmoL) and potassium carbonate (3.1 g; 22.4 mmoL) in acetone (30 mL) was refluxed for 6.5 hours and then cooled to room temperature. The reaction mixture was filtered and the cake was washed forward with acetone. The filtrate was concentrated and dried under high vacuum to give 4.5 g of intermediate 2 (having a methyl ester acetate) that was carried forward without purification. Methanol/water mixture (16 mL/16 mL) was added to intermediate 2 and potassium hydroxide (0.63 g; 15.8 mmoL). The reaction mixture was refluxed for 2 hours then cooled to room temperature. Aqueous 2M hydrochloric acid (10 mL) was added to adjust the pH to 1-2. The slurry was stirred overnight, filtered and washed with a mixture of methanol/water (40 mL, 1:1) and 2×10 mL water. The solid was dried under vacuum to give Treprostinil as a white solid (4.0 g; 90%).

Example 2

Treprostinil Sodium Salt Preparation

A 100 ml round bottom flask was charged with Treprostinil (1.021 g, 2.61 mmol) followed by 25 ml acetone. This solution was warmed up to 30° C. and added of 5M Sodium hydroxide (0.61 ml, 3.05 mmol) dropwise while maintaining an internal temperature below 30° C. The pH of the solution was maintained at 8-9. After 15 minutes under agitation, a fiber like solid began to crystallize from the reaction mixture. The mixture was stirred for 1 hour at room temperature then cooled to 0-5° C. and stirred at this temperature for another hour. The solid was collected by vacuum filtration, rinsed with acetone and dried under vacuum overnight to yield 0.95 g of a white solid. (purity: 99.67% by HPLC; yield: 88%; Sodium content (ICP): 6.05% w/w). Powder X-ray diffraction spectra of the treprostinil sodium is shown in FIG. 1.

The invention claimed is:

1. A process for preparing a treprostinil salt, comprising:
dissolving treprostinil in a solvent, wherein the solvent consists essentially of a water-miscible organic solvent, to form a treprostinil solution, wherein the water-miscible organic solvent is selected from a water-miscible ketone, a water-miscible ether or acetonitrile;
reacting the treprostinil solution with an aqueous basic solution containing an alkali metal cation to form a reaction mixture containing the treprostinil salt;
allowing crystallization of the treprostinil salt; and
collecting the treprostinil salt formed.

2. The process according to claim 1, wherein the water-miscible organic solvent is a hydrocarbon based water-miscible ketone solvent.

3. The process according to claim 1, wherein the water-miscible ketone solvent is a linear or branched alkyl ketone.

4. The process according to claim 1, wherein the water-miscible ketone solvent is acetone.

5. The process according to claim 1, wherein the water-miscible organic solvent is tetrahydrofuran.

6. The process according to claim 1, wherein ratio of treprostinil to the water-miscible organic solvent is 1 g of treprostinil to from 5 to 100 mL of the water-miscible organic solvent.

7. The process according to claim 1, wherein ratio of treprostinil to the water-miscible organic solvent is 1 g of treprostinil to from 15 to 50 mL of the water-miscible organic solvent.

8. The process according to claim 1, wherein the aqueous basic solution contains hydroxide, carbonate or bicarbonate anion.

9. The process according to claim 1, wherein the alkali metal cation is lithium, sodium or potassium.

10. The process according to claim 1, wherein the alkali metal cation is sodium.

11. The process according to claim 1, wherein the aqueous basic solution contains sodium hydroxide.

12. The process according to claim 1, wherein the base in the aqueous basic solution has a concentration of from about 2 to about 8 molar.

13. The process according to claim 1, wherein the base in the aqueous basic solution has a concentration of about 5 molar.

14. The process according to claim 1, wherein mole ratio of base in the aqueous basic solution to treprostinil ranges from 1:1 to 2:1.

15. The process according to claim 1, wherein mole ratio of base in the aqueous basic solution to treprostinil is about 1.1:1.

16. The process according to claim 1, wherein volumetric ratio of the water-miscible organic solvent to the aqueous basic solution is from 10:1 to 70:1.

17. The process according to claim 1, wherein volumetric ratio of the water-miscible organic solvent to the aqueous basic solution is about 40:1.

18. The process according to claim 1, wherein the treprostinil salt is treprostinil sodium.

19. The process according to claim 1, further comprising warming the treprostinil solution up to about 60° C. prior to reacting it with the aqueous basic solution.

20. The process according to claim 1, further comprising warming the treprostinil solution up to about 30° C. prior to reacting it with the aqueous basic solution.

21. The process according to claim 1, wherein the aqueous basic solution is added to the treprostinil solution for reaction therewith.

22. The process according to claim 1, wherein the reaction of the treprostinil solution with the aqueous basic solution is carried out at an internal temperature below about 60° C.

23. The process according to claim 1, wherein the reaction of the treprostinil solution with the aqueous basic solution is carried out at an internal temperature below about 30° C.

24. The process according to claim 1, wherein the reaction of the treprostinil solution with the aqueous basic solution is agitated.

25. The process according to claim 1, wherein after allowing crystallization of treprostinil salt, the reaction mixture is agitated for at least about 4 hours.

26. The process according to claim 1, wherein after allowing crystallization of the treprostinil salt, the reaction mixture is agitated for about 1 hour.

27. The process according to claim 25, wherein the agitation is carried out at room temperature.

28. The process according to claim 1, further comprising cooling the reaction mixture from 0 to 15° C. prior to collecting the crystals.

29. The process according to claim 1, further comprising cooling the reaction mixture from 0 to 5° C. prior to collecting the crystals.

30. The process according to claim 28, further comprising agitating the reaction mixture during cooling.

31. The process according to claim 30, wherein the solution is cooled and agitated for about 5 hours.

32. The process according to claim 31, wherein the solution is cooled and agitated for about 1 hour.

33. The process according to claim 1, wherein the treprostinil salt is collected by vacuum filtration.

34. The process according to claim 1, wherein the treprostinil salt collected is dried.

* * * * *